United States Patent [19]
Wilson et al.

[11] Patent Number: 5,354,201
[45] Date of Patent: Oct. 11, 1994

[54] DENTURE RETAINING DEVICES

[76] Inventors: Christopher M. Wilson, R.R. 2, Box 1230, Morrisville, Vt. 05661; Bryan S. Booth, R.R. 1, Box 710, Bethel, Vt. 05032

[21] Appl. No.: 163,751
[22] Filed: Dec. 7, 1993
[51] Int. Cl.$^5$ .................. A61C 13/12; A61C 13/225; A61C 13/02
[52] U.S. Cl. .................. 433/177; 433/168.1
[58] Field of Search .................. 433/168.1, 169, 177, 433/199.1

[56] References Cited
U.S. PATENT DOCUMENTS

| | | | |
|---|---|---|---|
| 1,153,486 | 9/1915 | Gregg | 433/177 |
| 1,732,899 | 10/1929 | Krasnoff | 433/177 |
| 1,924,265 | 8/1933 | Wharton . | |
| 1,947,026 | 2/1934 | Wharton . | |
| 2,250,373 | 7/1941 | Hagerman | 433/177 |
| 3,094,778 | 6/1963 | Mailland | 433/177 |
| 3,837,079 | 9/1974 | Cecero | 433/177 |
| 3,919,771 | 11/1975 | Ostermann . | |
| 4,376,629 | 3/1983 | Ebeling . | |
| 4,923,795 | 5/1990 | Franklin . | |

Primary Examiner—Cary E. O'Connor
Assistant Examiner—Nicholas D. Lucchesi
Attorney, Agent, or Firm—Richard C. Litman

[57] ABSTRACT

Dental appliances, including dentures, which have flange extensions attached through elastically hinged sections provide added stability and security during mastication by redistributing forces to an increased surface area, and advantageously utilizing underlying intraoral bone ridges. The hinged sections allow these appliances to be installed and removed over these bone ridges. The hinged sections are biased so as to return to their original configuration once in place. Smooth conforming surfaces in contact with tissue allow these appliances to be comfortably used. Lower dentures in particular are advantageously equipped with extended flanges which are attached through hinges at the mylohyoid ridges and redistribute forces from frontal loads across the mylohyoid ridges to the submandibular fossae.

20 Claims, 4 Drawing Sheets

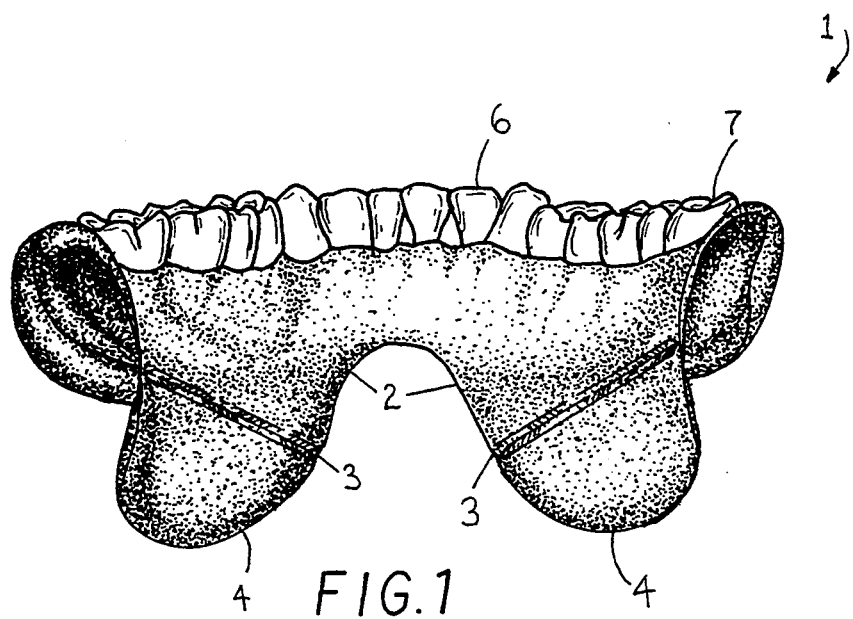
FIG. 1
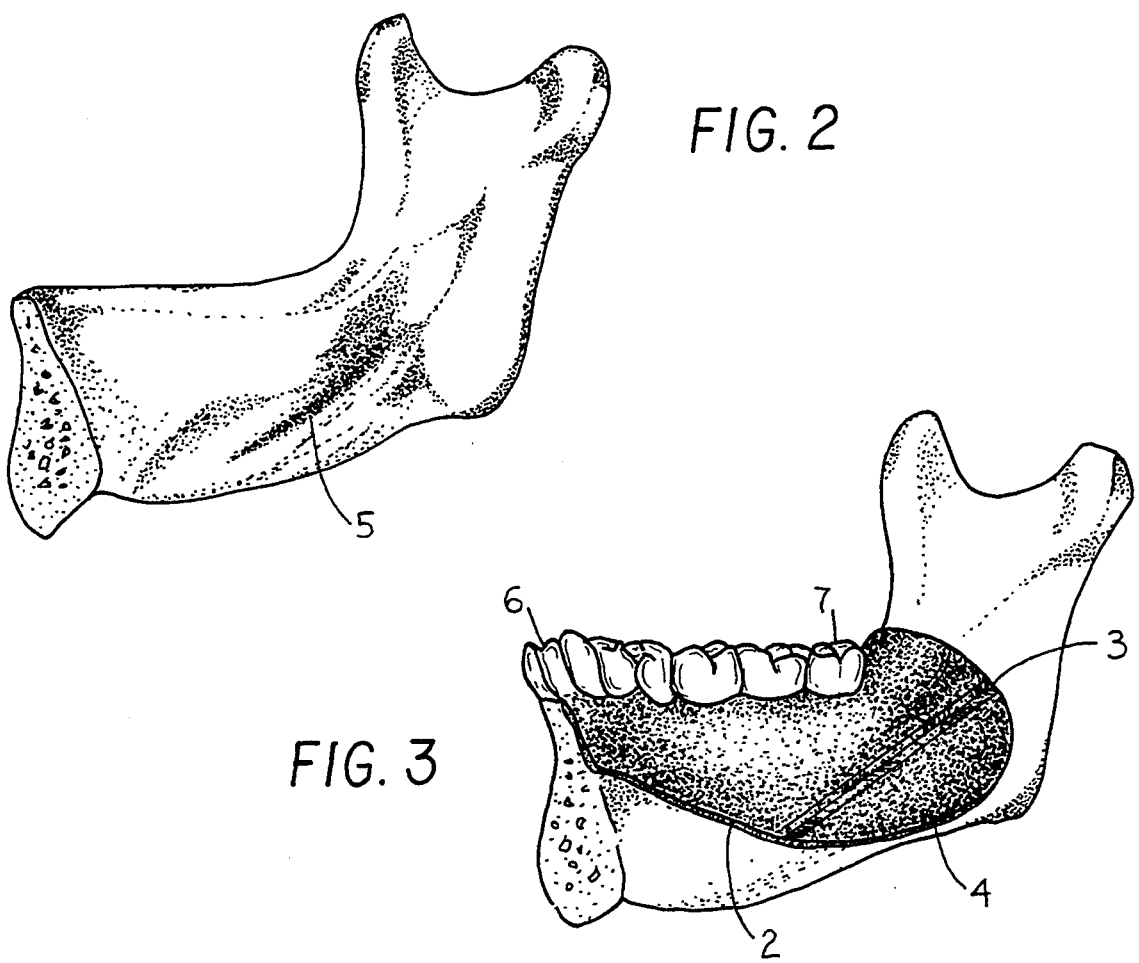
FIG. 2
FIG. 3

DENTURE RETAINING DEVICES

BACKGROUND OF THE INVENTION

1. Field of the Invention

The present invention relates generally to devices for retaining flanged dental appliances in position. More particularly, the present invention relates to dentures having flexibly mounted flange extensions which aids in their retention and stabilization.

2. Description of the Prior Art

Presently, conventional dentures or the like, especially mandibular and distal extension partial dentures are predominantly designed to be placed over the gums, and generally rely on gravity, tooth clasps, and/or adhesives to retain and secure them in place. Various denture retaining devices are available in the prior art, but have up to now met with limited success. For instance, U.S. Pat. Nos. 1,924,265 and 1,947,026 to Wharton disclose three piece lower dentures wherein two side pieces extend lower than a middle piece. Upon placement in the mouth, the pieces are attached together through interlocking tongue and groove or other construction which allow movement in a vertical direction. Besides the relative difficulty in maneuvering the three pieces in the user's mouth, any sufficient force on the central piece of these dentures from incisor load may not be effectively transferred to the side pieces. This may lead to shear separation of the connections between the central piece and side pieces.

U.S. Pat. No. 3,919,771 to Ostermann discloses a device for retaining a lower denture having an externally attached fixed element, a retaining tongue which slides within the fixed element, and a cover piece which covers the fixed element and a portion of the retaining tongue. To use this device, the fixed element is secured to a lower denture such that the retaining tongue slides downward. After placement in the mouth, the user must slide the tongue below the mylohyoid ridge, then place the cover piece to secure the retaining tongue in position. Besides the necessity for complex user manipulation, this device applies pressure to the cavity below the mylohyoid ridge on a relatively small surface area. Further, the protruding structure of this device may lead to irritation and abrasion, thereby reducing the comfort with which the attached denture may be worn.

U.S. Pat. Nos. 4,376,629 to Ebeling and 4,923,795 to Franklin disclose flexible dentures which grip the gums of users. However, these dentures do not extend below the mylohyoid ridge or any other like bone ridges to provide support.

None of the above inventions and patents, taken either singly or in combination, is seen to describe the instant invention as claimed.

SUMMARY OF THE INVENTION

The present invention is drawn to flanged dental appliances which have incorporated therein a device which aids in retaining and stabilizing the appliances. The device includes hinging sections, and thickened flange extensions attached to the hinging sections. These hinging sections are attached to an interior flange of dental appliances so as to be positioned to lie along bone ridges, such as the mylohyoid ridges. Mechanisms or materials for providing positional memory cooperate within these hinging sections, thereby allowing the flanges to be flexed medially during insertion or extraction of the appliance. Once in place, the flange extensions hingedly return to their original configuration, settling into a fossa proximate to the bone ridge. This spreads equal pressure onto the extended surface area of the fossa proximate to the bone ridge to stabilize the appliance incorporating the present device. The stabilized appliance of the present invention will also resist dislodgement under load by redistributing forces across a bone ridge or ridges.

The present device is advantageously incorporated into dentures such that a smooth surface is presented to all underlying and contacting tissue. The present invention preferably uses semi-rigid polymeric materials to provide biasing, positional memory, and smooth surface contact in and around the hinging sections. Semi-rigid materials may also provide the required hinging mechanism through which the appliance may be installed and removed. Optionally incorporated hinging structures, such as a spring loaded hinge or living hinges such as a scored polypropylene sheet, may be employed in the present invention to bolster flexibility, and/or positional memory. Further, when more than one flange extension is used across symmetric bone ridges, any applied force can be more effectively distributed, and the stabilizing effect is increased.

Accordingly, it is a principal object of the invention to provide a device which allows dental appliances, especially mandibular and lower distal partial dentures, to be stabilized and secured in place by resisting dislodgement.

It is another object of the invention to provide improved dentures which advantageously incorporate the present device.

It is yet another object of the invention to provide stable dentures having smooth conforming surfaces which are comfortable to wear.

Still further, an object of the invention is to provide devices which allow the user to consume a wider variety of foods with confidence.

These and other objects of the present invention will become readily apparent upon further review of the following description and drawings.

BRIEF DESCRIPTION OF THE DRAWINGS

FIG. 1 is a posterior view of lower dentures according to the present invention.

FIG. 2 is a side cut-away view of the right jaw, showing the right mylohyoid ridge.

FIG. 3 is a side cut-away view of the right jaw, showing the lower denture of FIG. 1 in position.

Similar reference characters denote corresponding features consistently throughout the attached drawings.

DETAILED DESCRIPTION OF THE PREFERRED EMBODIMENTS

Figure 4:
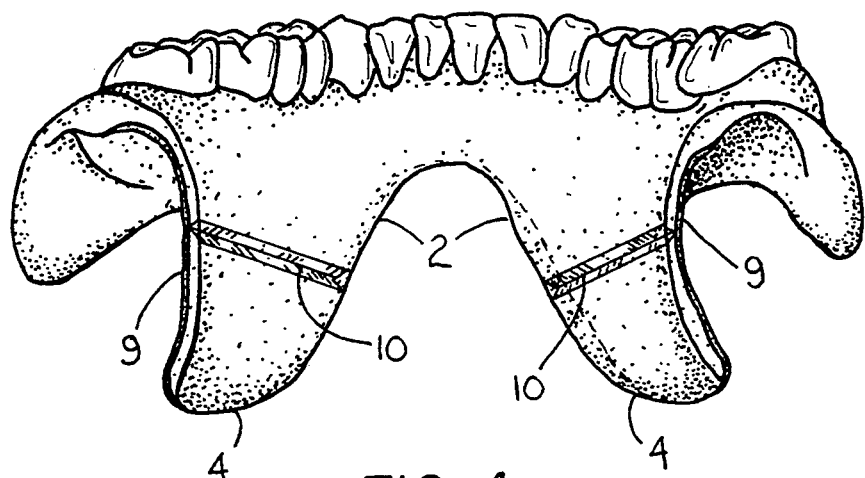
FIG. 4 is a posterior perspective view of lower dentures according to a preferred embodiment of the present invention.

The present invention is advantageously applied in lower dentures as shown in FIG. 1. The present denture as a whole is designated reference numeral 1, and includes an upper section 2 including flanged sections, hinging areas 3, and flange extensions 4. Upper section 2 incorporates analogous elements of conventional dentures. In FIG. 1, upper section 2 includes teeth such as incisors 6 and molars 7.

The present invention may be used to secure and stabilize appliances across any underlying substantially straight section of an intraoral bone ridge, and is particularly advantageous when used across the mylohyoid ridge 5, as shown in FIG. 2. Preferably, two devices according to the present invention are advantageously positioned over both mylohyoid ridges 5, with the flange extensions 4 applying slight pressure to the tissue of the submandibular fossae under the mylohyoid ridge, as seen in FIG. 3.

The interior of a flanged denture useful in the present invention, which contacts the tissue of the mouth, is shaped to conform to the individual user, being the complimentary shape of substantially all features of the user's intraoral tissue that the denture will overlay. This may be accomplished by making a cast of the user's mouth. The cast preparation may be accomplished with readily available materials and techniques with the stipulation that the tissue over which flange extensions 4 will be positioned must be included in the casting. Preferred materials for making the cast include gypsum, resin, silicone, and rubber. Preferred techniques for making the cast include forming a dental impression, using these materials to create a mold, which is then poured with a thermal setting modeling composition.

The resultant model of the user's mouth is then prepared before creating the appropriate flanged appliance. Areas on the model that correspond to the tissue over which flange extensions 4 will be positioned is relieved or shaved. Preferably, from 0.2 to 1 mm is relieved from these areas. Most preferably, from 0.25 to 0.50 mm is relieved. For example, in appliances such as lower dentures where the bone ridges used are the mylohyoid ridges, the area relieved corresponds to the tissue overlying the submandibular fossae.

The appropriate flanged appliance of the present invention is then manufactured on the model. Preferably, hard denture base is use to create the foundation of the appliance. Preferred materials for the denture base include hard acrylics, such as methyl methacrylate with a low water content, vinyl, and silicone. The hard denture base may be textured or detailed to simulate gums and like tissue where appropriate. In lower dentures 1, upper section 2 and flanges 4 are most preferably created unitarily from hard acrylic, and teeth 6 and 7 are inserted or rendered on upper section 2.

The hinging section 3 may then be created. The considerations important in the creation of the hinging section include: 1) sufficient freedom of movement such that the attached flange extension may in one state be positioned to apply pressure against the tissue overlying a target fossa, and in a second state be unrestricted by any bone ridge; 2) positional memory for at least the above first state, such that once installed, the attached flange extensions will reposition to exert the necessary pressure in cooperation with the appliance as a whole, and will distribute forces across the height of contour over which the hinging section rests; and 3) the hinging section should remain smooth to the tissue, having no fissures or sharp protrusions to irritate and/or lacerate tissue.

Disparate elements may be used to provide the necessary functionalities. A biasing mechanism can be used to urge the flange extension to pivot about the hinging area in a direction towards the fossae proximate to the bone ridge, having a stop when the flange extension reaches the first state, and flexible materials incorporated into the hinging ares to cover the biasing mechanism. Alternatively, the necessary functionalities may be met by the inherent resilience in the materials incorporated into the hinging areas or by a combination of both.

Figure 9:
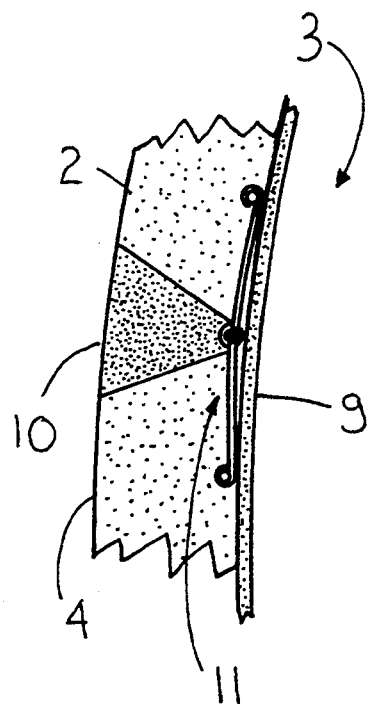
FIG. 9 is a side partial sectional view of a hinging section incorporating an optional hinging mechanism according to the present invention.
Figure 10:
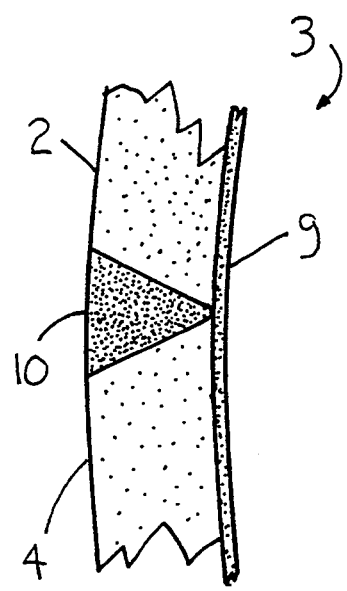
FIG. 10 is a side partial sectional view of a hinging section according to one embodiment of the present invention.
Figure 11:
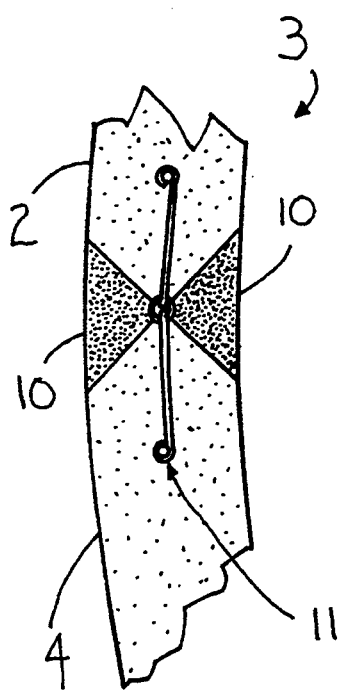
FIG. 11 is a side partial sectional view of a hinging section according to another embodiment of the present invention.

As can be seen best in FIGS. 9–11, a portion of upper section 2 corresponding to the interior part of a flange which lies along the gums of the mouth, and the flange extension 4, in the first state meet at a line which is substantially over and parallel to the line demarcated by a substantially linear bone ridge. This configuration may be achieved by forming 2 and 4 unitarily, then cutting a groove or grooves through the unitary piece to form the separate parts. Alternatively, 2 and 4 may be formed separately, having angled edges. The angle defined by the cut sides of the groove, or the angled edges of 2 and 4, is preferably between 30 and 100 degrees, being preferably about 35–50 degrees when a single groove is cut, as shown in FIG. 9 and about 35–90 degrees when two grooves are cut, as shown in FIG. 11.

Figure 6:
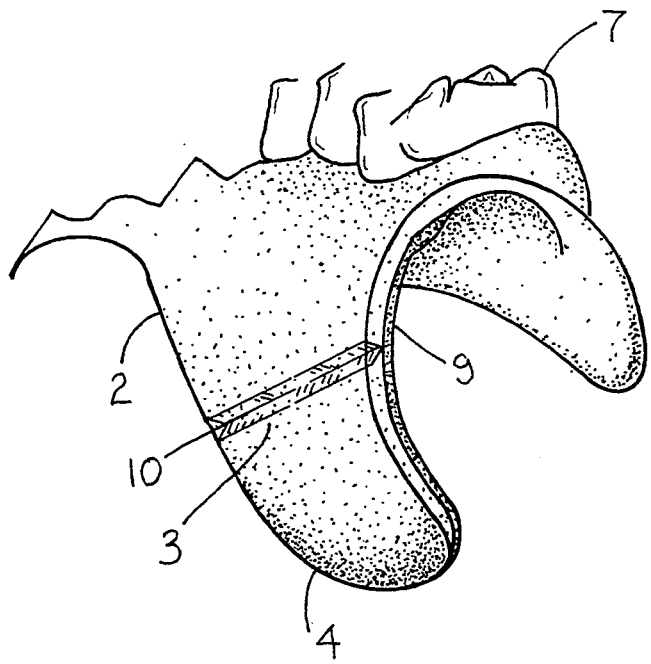
FIG. 6 is a partial side perspective view of lower dentures according to one embodiment of the present invention.
Figure 7:
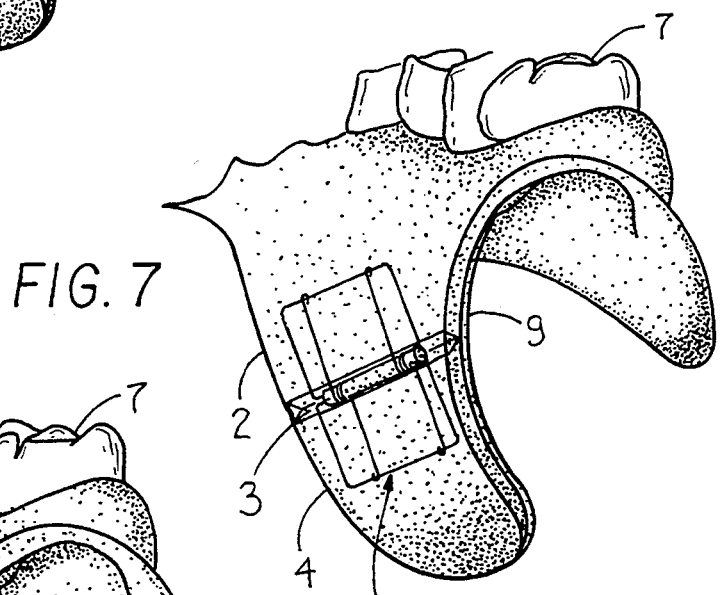
FIG. 7 is a partial side perspective view of lower dentures incorporating a spring loaded hinge.
Figure 8:
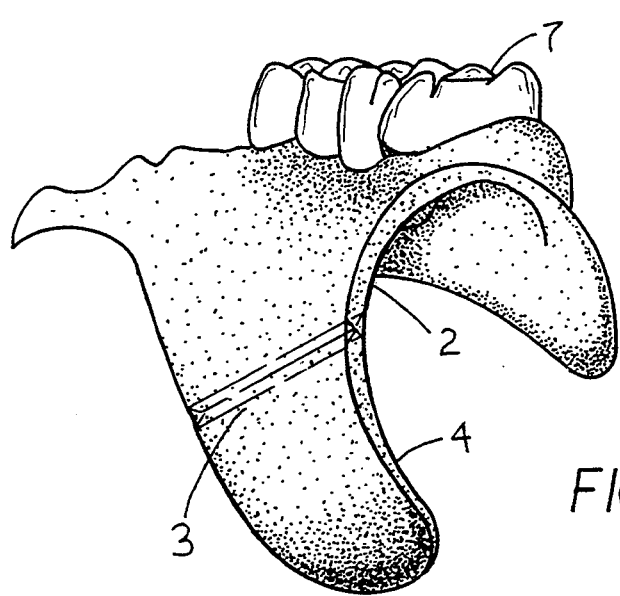
FIG. 8 is a partial side perspective view of lower dentures according to another embodiment of the present invention.

Preferred constructions of the hinged section utilize semi-rigid materials in a wedge or wedges 10 filled in between upper section 2 and flange extension 4. Further, to enhance the positional memory across the hinged section, an additional liner of semi-rigid material 9 may be applied to the inside surface around the hinged area to provide biasing. Liner 9 may run along the full height of the appliance, as shown in FIGS. 6 and 7, or be substantially located only in the hinged section. The denture base material of 2 and 4 may be relieved to accommodate liner 9, or the liner may be cast prior to 2 and 4 upon the model of the users mouth.

The passive, semi-rigid materials used in wedge 10 and liner 9 include any intraorally acceptable polymeric material which preferably has sufficient elasticity that a user may flex the hinged section to the second state, yet have sufficient rigidity to maintain the first state under typical loads for the appliance. A device such as disclosed by Eckland, U.S. Pat. No. 5,055,041 may be used to determine the necessary characteristics of the material. Preferably, the material is an acrylic. Most preferably, the material is a methyl methacrylate, with higher water content than used in a hard denture base. The use of methyl methacrylate is desirable, since its rigidity and elasticity may be altered by the level of hydration in curing. When both the wedge material 10 and liner 9 is used in the hinged area, the wedge material is preferably less rigid than the liner material. As the denture base may also be made from methyl methacrylate with a low water content, the materials necessary for the instant invention ar readily available in this most preferred embodiment.

Figure 5:
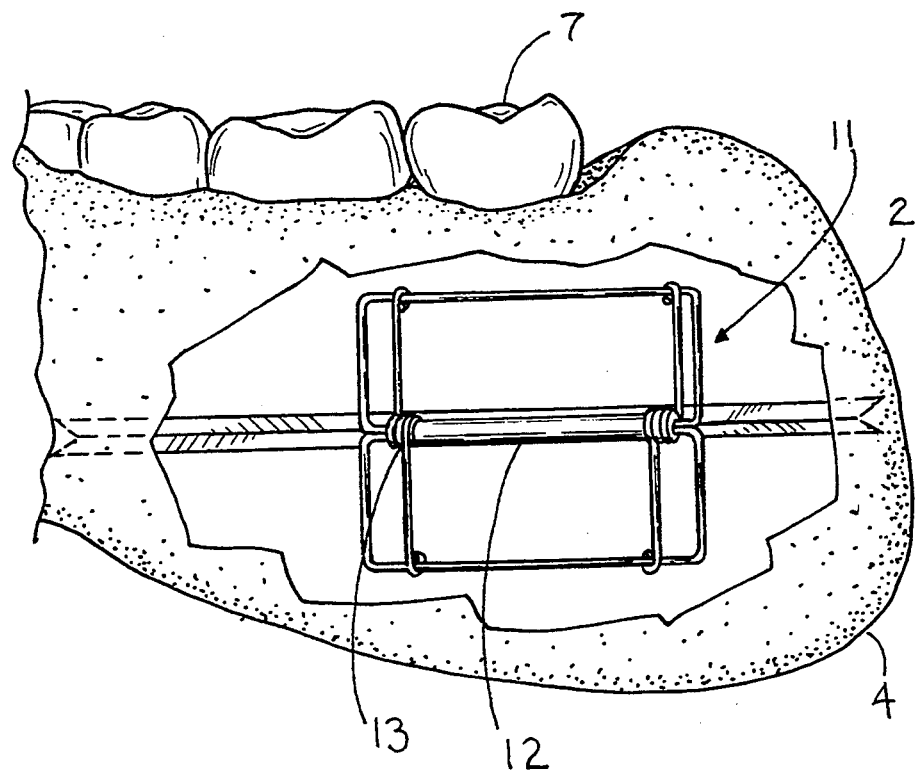
FIG. 5 is a side cutout view of lower dentures incorporating an optional spring loaded hinge.

Optionally, further mechanisms 11 may be used to enhance the positional memory of the hinging section. These may be used in conjunction with liner 9, as shown in FIG. 9 or without a liner, as shown in FIG. 11. The mechanism 11 may be of the spring loaded biasing type having hinge 12, spring 13, and biasing members as shown in FIG. 5. This type of mechanism when utilized should be made from biocompatible materials, such as surgical steel, and have an axis of hinging action substantially along the line demarcated by the underlying bone ridge. Preferably, these mechanisms are embedded into the denture base material of 2 and 4 prior to hardening of the base material.

Other mechanisms 11 may be used including living hinges, such as a rigid sheet of polypropylene or like crystalline plastic which is scored along the hinging axis. This type of mechanism may be embedded in the denture base material of 2 and 4, in substantially the same manner as the spring loaded biasing type. Holes may be provided on both sides of the score line such that the denture base material, as it cures, fixes the position of the mechanism. When mechanisms 11 are used to provide the positional memory and/or hinging action, the requirements on materials filling wedges 10 and liner 9 may be relaxed, as they no longer need to supply the transferred functionality. Accordingly, a wider range of materials may be used, the important consideration being the ability to provide a smooth surface for contacting tissue throughout the motion of the embedded mechanism.

EXAMPLE 1

An alginate impression of a patient's mouth was made in the dentist chair which extended into the lingual sulcus. A custom tray was then fabricated in the lab, extending 3 mm from the sulcus in the lingual area. The custom tray was then fitted to the alveolar ridge, being trimmed and boarder molded as needed. While the impression making and fitting were performed, the patient was instructed to open his/her mouth to its fullest extent, and to place their tongue against the palate. Any displacement caused by this is corrected. The impression is then corrected with the modified custom tray. The resultant corrected impression was then poured in the lab to form a model of the patient's mouth in dental stone, and allowed to set. One to two millimeters was relieved from the area representing both the submandibular fossae in equal amounts. A mandibular denture was created on the model from methyl methacrylate denture base. 45° V shaped grooves were cut along both of the mylohyoid ridges, separating the denture into an upper section, and two flange extensions. Methyl methacrylate having a higher water content was filled into the grooves, and along the surface around the groove on the tissue contacting side of the denture. A mixture of 4:8 liquid to methyl methacrylate powder was used in the groove, and 4:10 liquid to powder was used along the contacting surface.

CASE A

A ninety-five year old woman upon losing her conventional lower denture was fitted with a mandibular denture according to Example 1. The patient had worn dentures for over fifty years, and the anterior portion of her mandibular alveolar ridge had resorbed to the point of almost being flat, leading to the instability and loss of her conventional dentures. Despite this, the improved stability of the dentures prepared according to the present invention allowed the patient to continue to wear lower dentures.

CASE B

A sixty year old man with an edentulous mandibular ridge had previously been unable to tolerate conventional lower dentures. After fitting the patient with mandibular dentures according to Example 1, the patient was able to immediately eat an apple without causing dislodgement of the dentures.

It is to be understood that the present invention is not limited to the embodiments described above, but encompasses any and all embodiments within the scope of the following claims.

We claim:

1. A denture comprising:
   a body portion formed from a substantially rigid material, including at least one rigid flanged section shaped to cover gums in a mouth, said flanged section having at least one bevelled face adjacent to an edge thereof;
   at least one rigid flange extension formed from a substantially rigid material, having one side shaped to contact intraoral tissue overlying a fossa proximate to a substantially linear bone ridge inside the mouth, and having at least one bevelled face adjacent to an edge thereof;
   means for hingedly attaching said flanged section of said body portion to said flange extension such that said at least one bevelled face adjacent said edge of said flanged section is adjacent to said at least one bevelled face adjacent said edge of said flange extension;
   wherein said bevelled faces of said flanged section and said flange extension define at least one groove;
   wherein said means for hingedly attaching said flanged section to said flange extension includes at least one substantially resilient wedge disposed inside said at least one groove, whereby said flanged section of said body portion and said flange extension are hingedly attached.

2. The denture according to claim 1, wherein said at least one groove is located on a surface of said denture which is not in contact with the gum of the mouth.

3. The denture according to claim 1, wherein said at least one groove is located on a surface of said denture which is in contact with the gum of the mouth.

4. The denture according to claim 1, wherein each of said flanged section and said flange extension have two bevelled faces, wherein said bevelled faces define two grooves when said flanged section and said flange extension are hingedly attached, said hinged attachment means including at least one substantially resilient wedge disposed inside each of said grooves.

5. The denture according to claim 4, further comprising an additional biasing means to enhance positional memory of said hinged attachment means.

6. The denture according to claim 5, wherein said additional biasing means includes a spring loaded hinge spanning said hinged attachment means between said flanged section and said flange extension, said spring-loaded hinge being embedded within said flanged section and said flange extension.

7. The denture according to claim 5, wherein said additional biasing means includes a living hinge spanning said hinged attachment means between said flanged section and said flange extension.

8. The denture according to claim 7, wherein said living hinge is a rigid sheet of polypropylene.

9. The denture according to claim 1, further comprising a flexible lining interposed between the gum and said denture, said lining in continuous contact with said flanged section and said flange extension.

10. The denture according to claim 9, further comprising an additional biasing means to enhance positional memory of said hinged attachment means, wherein said additional biasing means is selected from the group consisting of a spring-loaded hinge and a living hinge, said additional biasing means spanning said hinged attachment means between said flanged section and said flange extension, said additional biasing means being embedded within said flanged section and said flange extension.

11. The denture according to claim 10, wherein said additional biasing means includes a living hinge spanning said hinged attachment means between said flanged section and said flange extension.

12. The denture according to claim 11, wherein said living hinge is a rigid sheet of polypropylene.

13. The denture according to claim 9, further comprising an additional biasing means to enhance positional memory of said hinged attachment means, wherein said additional biasing means is interposed between said lining and said denture.

14. The denture according to claim 1, wherein said substantially rigid material forming said body portion, said flanged section, and said flange extension is selected from the group consisting of acrylic resins, vinyl resins, and silicone resins.

15. The denture according to claim 14, wherein said substantially rigid material is methyl methacrylate resin.

16. The denture according to claim 15, wherein said methyl methacrylate resin is methyl methacrylate denture base.

17. The denture according to claim 1, further comprising an additional biasing means to enhance positional memory of said hinged attachment means.

18. The denture according to claim 17, wherein said additional biasing means includes a spring-loaded hinge spanning said hinge attachment means between said flanged section and said flange extension.

19. The denture according to claim 17, wherein said additional biasing means includes a living hinge spanning said hinged attachment means between said flanged section and said flange extension.

20. The denture according to claim 19, wherein said living hinge is a rigid sheet of polypropylene.

* * * * *